;(12) United States Patent
Qi et al.

(10) Patent No.: US 7,378,204 B2
(45) Date of Patent: May 27, 2008

(54) PHOTOCONDUCTIVE MEMBER

(75) Inventors: Yu Qi, Oakville (CA); Nan-Xing Hu, Oakville (CA); Gregory McGuire, Mississauga (CA); Cheng-Kuo Hsiao, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 372 days.

(21) Appl. No.: 11/153,663

(22) Filed: Jun. 15, 2005

(65) Prior Publication Data

US 2006/0286472 A1    Dec. 21, 2006

(51) Int. Cl.
G03G 15/02    (2006.01)
C07C 211/00    (2006.01)

(52) U.S. Cl. .............. 430/58.75; 430/58.85; 430/59.5; 430/60; 564/431

(58) Field of Classification Search ........... 430/58.7, 430/58.75, 58.85, 59.5, 60
See application file for complete search history.

(56) References Cited

U.S. PATENT DOCUMENTS

| | | | |
|---|---|---|---|
| 4,265,990 A | 5/1981 | Stolka et al. | |
| 4,921,769 A | 5/1990 | Yuh et al. | |
| 5,473,064 A | 12/1995 | Mayo et al. | |
| 5,482,811 A | 1/1996 | Keoshkerian et al. | |
| 5,521,043 A | 5/1996 | Listigovers et al. | |
| 5,521,306 A * | 5/1996 | Burt et al. | 540/141 |
| 6,015,645 A | 1/2000 | Murti et al. | |
| 6,156,468 A | 12/2000 | Wehelie et al. | |
| 6,177,219 B1 | 1/2001 | Yuh et al. | |
| 6,255,027 B1 | 7/2001 | Wehelie et al. | |
| 2001/0031412 A1* | 10/2001 | Itami et al. | 430/58.15 |
| 2003/0175603 A1* | 9/2003 | Nakata et al. | 430/58.1 |
| 2004/0161683 A1 | 8/2004 | Wu et al. | |
| 2004/0202947 A1* | 10/2004 | Wu et al. | 430/59.4 |

* cited by examiner

*Primary Examiner*—Mark F. Huff
*Assistant Examiner*—Peter L Vajda
(74) *Attorney, Agent, or Firm*—E. O. Palazzo

(57) ABSTRACT

A photoconductive imaging member containing a photogenerating layer, and a charge transport layer, and wherein the charge transport layer is comprised of an arylamine containing a moiety that minimizes oxidation.

15 Claims, No Drawings

PHOTOCONDUCTIVE MEMBER

CROSS-REFERENCE TO RELATED APPLICATIONS

There is illustrated in U.S. Pat. No. 7,037,631, entitled Photoconductive Imaging Members, the disclosure of which is totally incorporated herein by reference, a photoconductive imaging member comprised of a supporting substrate, a hole blocking layer thereover, a crosslinked photogenerating layer and a charge transport layer, and wherein the photogenerating layer is comprised of a photogenerating component and a vinyl chloride, allyl glycidyl ether, hydroxy containing polymer.

A number of the components of the above copending application, such as the supporting substrates, resin binders, and photogenerating layer components may be selected for the member of the present disclosure in embodiments thereof.

RELATED PATENTS

Illustrated in U.S. Pat. No. 6,015,645, the disclosure of which is totally incorporated herein by reference, is a photoconductive imaging member comprised of a supporting substrate, a hole blocking layer, an optional adhesive layer, a photogenerator layer, and a charge transport layer, and wherein the blocking layer is comprised, for example, of a polyhaloalkylstyrene.

Illustrated in U.S. Pat. No. 5,473,064, the disclosure of which is totally incorporated herein by reference, is a process for the preparation of hydroxygallium phthalocyanine Type V, essentially free of chlorine, whereby a pigment precursor Type I chlorogallium phthalocyanine is prepared by reaction of gallium chloride in a solvent, such as N-methylpyrrolidone, present in an amount of from about 10 parts to about 100 parts, and preferably about 19 parts with 1,3-diiminoisoindolene ($DI^3$) in an amount of from about 1 part to about 10 parts, and preferably about 4 parts $DI^3$, for each part of gallium chloride that is reacted; hydrolyzing the pigment precursor chlorogallium phthalocyanine Type I by standard methods, for example acid pasting, whereby the pigment precursor is dissolved in concentrated sulfuric acid and then reprecipitated in a solvent, such as water, or a dilute ammonia solution, for example from about 10 to about 15 percent; and subsequently treating the resulting hydrolyzed pigment hydroxygallium phthalocyanine Type I with a solvent, such as N,N-dimethylformamide, present in an amount of from about 1 volume part to about 50 volume parts, and preferably about 15 volume parts for each weight part of pigment hydroxygallium phthalocyanine that is used by, for example, ballmilling the Type I hydroxygallium phthalocyanine pigment in the presence of spherical glass beads, approximately 1 millimeter to 5 millimeters in diameter, at room temperature, about 25° C., for a period of from about 12 hours to about 1 week, and preferably about 24 hours.

Illustrated in U.S. Pat. No. 5,521,043, the disclosure of which is totally incorporated herein by reference, are photoconductive imaging members comprised of a supporting substrate, a photogenerating layer of hydroxygallium phthalocyanine, a charge transport layer, a photogenerating layer of BZP perylene, which is preferably a mixture of bisbenzimidazo(2,1-a-1',2'-b)anthra(2,1,9-def:6,5,10-d'e'f')diisoquinoline-6,11-dione and bisbenzimidazo(2,1-a:2',1'-a)anthra(2,1,9-def:6,5,10-d'e'f')diisoquinoline-10,21-dione, reference U.S. Pat. No. 4,587,189, the disclosure of which is totally incorporated herein by reference; and as a top layer a second charge transport layer.

The appropriate components and processes of the above patents may be selected for the present disclosure in embodiments thereof.

BACKGROUND

This disclosure is generally directed to imaging members, and more specifically, the present disclosure is directed to single and multi-layered photoconductive imaging members comprised of a charge transport layer containing a charge transport component or compounds, especially hole transport components comprising both transport like an aryl amine and antioxidant functionalities to thus enable both charge transporting and antioxidant characteristics for the charge transport layer. The charge, and more specifically, hole transport layer can be comprised of molecules comprised of a tertiary arylamine and phenol components, and which molecules can be prepared, for example, by the condensation of a bis(hydroxyalkyl)-triarylamine and a phenol in the presence of an acid catalyst, and wherein the generated molecules are resistant to image deletion and also are protected from oxidation. Oxidation of hole transport molecules can cause lateral charge migration arising, for example, from poor corona charging resistance, and in addition components like antioxidents can escape from the charge transport layer when such layer is subjected to heat. The antioxidants illustrated herein can be added to the charge transport layer in an effective suitable amount, such as those amounts that would not adversely affect the electrical characteristics of the imaging member. The disadvantages of antioxidants escaping during, for example, heating, and high residue potentials are minimized, and in a number of instances avoided with the members of the present disclosure.

The members of the present disclosure may also contain a hole blocking layer, such as an undercoat layer (UCL) comprised of, for example, a metal oxide, such as titanium oxide dispersed in a phenolic resin/phenolic resin blend or a phenolic resin/phenolic compound blend, and which layer can be deposited on a supporting substrate. More specifically, the hole blocking layer in contact with the supporting substrate can be situated between the supporting substrate and the photogenerating layer, which is comprised, for example, of the photogenerating pigments of U.S. Pat. No. 5,482,811, the disclosure of which is totally incorporated herein by reference, especially Type V hydroxygallium phthalocyanine, and generally metal free phthalocyanines, metal phthalocyanines, perylenes, titanyl phthalocyanines, selenium, selenium alloys, azo pigments, squaraines, and the like. The imaging members of the present disclosure in embodiments exhibit a number of advantages as illustrated herein and excellent cyclic/environmental stability, and substantially no adverse changes in their performance over extended time periods; low and excellent $V_{low}$, that is the surface potential of the imaging member subsequent to a certain light exposure. The photoresponsive, or photoconductive imaging members can be negatively charged when the photogenerating layers are situated between the hole transport layer and the hole blocking layer deposited on the substrate.

Processes of imaging, especially xerographic imaging and printing, including digital, are also encompassed by the present disclosure. More specifically, the layered photoconductive imaging members of the present disclosure can be selected for a number of different known imaging and printing processes including, for example, electrophotographic imaging processes, especially xerographic imaging and printing processes wherein charged latent images are rendered visible with toner compositions of an appropriate charge polarity. The imaging members are in embodiments sensitive in the wavelength region of, for example, from about 500 to about 900 nanometers, and in particular from about 650 to about 850 nanometers, thus diode lasers can be selected as the light source. Moreover, the imaging members of this disclosure are useful in color xerographic applications, particularly high-speed color copying and printing processes.

REFERENCES

Layered photoresponsive imaging members have been described in numerous U.S. patents, such as U.S. Pat. No. 4,265,990, the disclosure of which is totally incorporated herein by reference, wherein there is illustrated an imaging member comprised of a photogenerating layer, and an aryl amine hole transport layer. Examples of photogenerating layer components include trigonal selenium, metal phthalocyanines, vanadyl phthalocyanines, and metal free phthalocyanines. Additionally, there is described in U.S. Pat. No. 3,121,006, the disclosure of which is totally incorporated herein by reference, a composite xerographic photoconductive member comprised of finely divided particles of a photoconductive inorganic compound dispersed in an electrically insulating organic resin binder.

There are disclosed in U.S. Pat. No. 3,871,882, the disclosure of which is totally incorporated herein by reference, photoconductive substances comprised of specific perylene-3,4,9,10-tetracarboxylic acid derivative dyestuffs. In accordance with this patent, the photoconductive layer is preferably formed by vapor depositing the dyestuff in a vacuum. Also, there are disclosed in this patent dual layer photoreceptors with perylene-3,4,9,10-tetracarboxylic acid diimide derivatives, which have spectral response in the wavelength region of from 400 to 600 nanometers. Further, in U.S. Pat. No. 4,555,463, the disclosure of which is totally incorporated herein by reference, there is illustrated a layered imaging member with a chloroindium phthalocyanine photogenerating layer. In U.S. Pat. No. 4,587,189, the disclosure of which is totally incorporated herein by reference, there is illustrated a layered imaging member with, for example, a perylene, pigment photogenerating component. Both of the aforementioned patents disclose an aryl amine component, such as N,N'-diphenyl-N,N'-bis(3-methyl phenyl)-1,1'-biphenyl-4,4'-diamine dispersed in a polycarbonate binder as a hole transport layer. The above components, such as the photogenerating compounds and the aryl amine charge transport, can be selected for the imaging members of the present disclosure in embodiments thereof.

In U.S. Pat. No. 4,921,769, the disclosure of which is totally incorporated herein by reference, there are illustrated photoconductive imaging members with blocking layers of certain polyurethanes.

Illustrated in U.S. Pat. Nos. 6,255,027; 6,177,219, and 6,156,468, the disclosures of which are totally incorporated herein by reference, are, for example, photoreceptors containing a hole blocking layer of a plurality of light scattering particles dispersed in a binder, reference for example, Example I of U.S. Pat. No. 6,156,468, the disclosure of which is totally incorporated herein by reference, wherein there is illustrated a hole blocking layer of titanium dioxide dispersed in a specific linear phenolic binder of VARCUM, available from OxyChem Company.

SUMMARY

It is a feature of the present disclosure to provide imaging members with many of the advantages illustrated herein, such as minimal dark injection, excellent photoinduced discharge characteristics, cyclic and environmental stability and acceptable charge deficient spot levels arising from dark injection of charge carriers.

Another feature of the present disclosure relates to the provision of layered photoresponsive imaging members, which are responsive to near infrared radiation of from about 700 to about 900 nanometers.

It is yet another feature of the present disclosure to provide layered photoresponsive imaging members with sensitivity to visible light.

Moreover, another feature of the present disclosure relates to the provision of layered photoresponsive imaging members containing hole transport layers comprised of components of a tertiary arylamine containing an antioxidant moiety to enable simultaneous hole transport and antioxidant characteristics.

In a further feature of the present disclosure there are provided imaging members containing, especially for drum photoreceptors, hole blocking polymer layers comprised of titanium oxide and a phenolic compound/phenolic resin blend, or a low molecular weight phenolic resin/phenolic resin blend, and which phenolic compounds containing at least two, and more specifically, two to ten phenolic groups or low molecular weight phenolic resins with a weight average molecular weight ranging from about 500 to about 2,000 can interact with and consume formaldehyde and other phenolic precursors within the phenolic resin effectively, thereby chemically modifying the curing processes for such resins and permitting, for example, a hole blocking layer with excellent efficient electron transport, and which usually results in a desirable lower residual potential and $V_{low}$.

Moreover, in another feature of the present disclosure there is provided a hole blocking layer comprised of titanium oxide, a phenolic resin/phenolic compound(s) blend or phenolic resin(s)/phenolic resin blend comprised of a first linear, or a first nonlinear phenolic resin and a second phenolic resin or phenolic compounds containing at least about 2, such as about 2, about 2 to about 12, about 2 to about 10, about 3 to about 8, about 4 to about 7, and the like, phenolic groups, and which blocking layer is applied to a drum of, for example, aluminum and cured at a high temperature of, for example, from about 135° C. to about 165° C.

Illustrated herein is a blocking layer comprised of phenolic compounds containing at least two, and more specifically, from about 2 to about 10, and yet more specifically, from about 4 to about 7 phenolic groups, such as bisphenol S, A, E, F, M, P, Z, hexafluorobisphenol A, resorcinol, hydroxyquinone, catechin, a lower molecular weight phenolic resin with a weight average molecular weight of from about 500 to about 2,000 blended with a phenolic resin containing phenolic groups, and wherein there results in a cured mixture about 95 to about 98 percent, or in embodiments up to 100 percent. The phenolic resins include formaldehyde polymers with phenol and/or cresol and/or p-tertbutylphenol and/or bisphenol A, such as VARCUM™ 29159 and 29112 (OxyChem Co.), DURITE™ P-97 (Borden Chemical) and AROFENE™ 986-Z1-50 (Ashland Chemical).

Aspects of the present disclosure relate to a photoconductive imaging member comprised of a supporting substrate, an optional hole blocking layer thereover, a photogenerating layer and a charge transport layer, and wherein the charge transport layer is comprised of novel resistant molecules with both triarylamine and phenol segments; a photoconductive imaging member comprised of a supporting substrate, a photogenerating layer, and a hole transport layer as illustrated herein, and wherein the transport layer can be generated from the condensation of a bis(hydroxymethyl)-triarylamine with a phenol in the presence of heat and in the presence of a catalyst, and wherein the photoconductive member resulting possesses excellent time zero potentials, and improved deletion resistance as illustrated hereinafter; a photoconductive imaging member wherein the photogenerator layer is of a thickness of from about 0.05 to about 10 microns; a photoconductive imaging member wherein the charge, such as hole transport layer, is of a thickness of from about 10 to about 50 microns; a photoconductive imaging member wherein the photogenerating layer is comprised of photogenerating pigments dispersed in a resinous binder in an amount of from about 5 percent by weight to about 95 percent by weight; a photoconductive imaging member wherein the photogenerating resinous binder is selected from the group consisting of copolymers of vinyl chloride, vinyl acetate and hydroxy and/or acid containing monomers, polyesters, polyvinyl butyrals, polycarbonates, polystyrene-b-polyvinyl pyridine, and polyvinyl formals and mixtures thereof in embodiments, a photoconductive imaging member comprised of a photogenerating layer, and a charge transport layer, and wherein the charge transport layer is comprised of an arylamine containing an antioxidant moiety; a compound of the formula

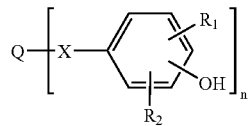

wherein Q represents a hole transporting aromatic tertiary amine moiety, X represents a divalent group, each R is a hydrogen atom, alkyl group or aryl, and n represents the number of groups; a photoconductive member comprised of a photogenerating component, and a charge transport comprised of hole transport molecules and a tertiary arylamine containing an antioxidant group or groups; a photoconductive imaging member wherein the aryl amine alkyl is methyl wherein halogen is chloride, and wherein the resinous binder is selected from the group consisting of polycarbonates and polystyrene; a photoconductive imaging member wherein the aryl amine is N,N'-diphenyl-N,N-bis(3-methyl phenyl)-1,1'-biphenyl-4,4'-diamine; alkylhydroxygallium, and wherein the photogenerating layer is comprised of phthalocyanines, hydroxygallium phthalocyanines, or a mixture thereof; and more specifically, Type V hydroxygallium phthalocyanine; wherein the hole blocking layer is comprised of cresol and phenol, a formaldehyde polymer generated with 4,4'-(1-methylethylidene)bisphenol; a formaldehyde polymer generated with cresol and phenol; and a formaldehyde polymer generated with phenol and p-tert-butylphenol; about 4 to about 50 weight percent of a phenolic compound; from about 1 to about 99 weight percent of a first phenolic resin and from about 99 to about 1 weight percent of a second phenolic resin, and wherein the total thereof is about 100 percent; the hole blocking layer is of a thickness of about 0.01 to about 30 microns; the hole blocking layer is comprised of a metal oxide, a blend of two phenolic resins and a dopant; and a hole blocking layer wherein the phenolic resin is comprised of a first resin that possesses a weight average molecular weight of from about 500 to about 2,000, and a second resin that possesses a weight average molecular weight of from about 2,500 to about 20,000, and wherein the blocking layer is provided on an aluminum drum followed by heat curing at a temperature of from about 135° C. to about 190° C.; the hole blocking or undercoat layers for the imaging members of the present disclosure contain a metal oxide like titanium, chromium, zinc, tin and the like, a mixture of phenolic compounds and a phenolic resin or a mixture of 2 phenolic resins, and optionally a dopant such as $SiO_2$. The phenolic compounds contain at least two phenol groups, such as bisphenol A (4,4'-isopropylidenediphenol), E (4,4'-ethylidenebisphenol), F (bis(4-hydroxyphenyl)methane), M (4,4'-(1,3-phenylenediisopropylidene)bisphenol), P (4,4'-(1,4-phenylene diisopropylidene)bisphenol), S (4,4'-sulfonyldiphenol), and Z (4,4'-cyclohexylidenebisphenol); hexafluorobisphenol A (4,4'-(hexafluoro isopropylidene)diphenol), resorcinol; hydroxyquinone, catechin and the like.

The hole blocking layer is, for example, comprised of from about 20 weight percent to about 80 weight percent, more specifically, from about 55 weight percent to about 65 weight percent of a metal oxide, such as $TiO_2$, from about 20 weight percent to about 70 weight percent, more specifically, from about 25 weight percent to about 50 weight percent of a phenolic resin, from about 2 weight percent to about 20 weight percent, more specifically, from about 5 weight percent to about 15 weight percent of a phenolic compound preferably containing at least two phenolic groups, such as bisphenol S, and from about 2 weight percent to about 15 weight percent, more specifically, from about 4 weight percent to about 10 weight percent of a plywood suppression dopant, such as $SiO_2$. The hole blocking layer coating dispersion can, for example, be prepared as follows. The metal oxide/phenolic resin dispersion is first prepared by ball milling or dynomilling until the median particle size of the metal oxide in the dispersion is less than about 10 nanometers, for example from about 5 to about 9. To the above dispersion, a phenolic compound and dopant are added followed by mixing. The hole blocking layer coating dispersion can be applied by dip coating or web coating, and the layer can be thermally cured after coating. The hole blocking layer resulting is, for example, of a thickness of from about 0.01 micron to about 30 microns, and more specifically, from about 0.1 micron to about 8 microns. Examples of phenolic resins include formaldehyde polymers with phenol, p-tert-butylphenol, cresol, such as VARCUM™ 29159 and 29101 (OxyChem Company) and DURITE™ 97 (Borden Chemical), formaldehyde polymers with ammonia, cresol and phenol, such as VARCUM™ 29112 (OxyChem Company), formaldehyde polymers with 4,4'-(1-methylethylidene)bisphenol, such as VARCUM™ 29108 and 29116 (OxyChem Company), formaldehyde polymers with cresol and phenol, such as VARCUM™ 29457 (OxyChem Company), DURITE™ SD-423A, SD-422A (Borden Chemical), or formaldehyde polymers with phenol and p-tert-butylphenol, such as DURITE™ ESD 556C (Border Chemical).

Examples of the charge transport components and molecules are illustrated with reference to the following formula wherein Q represents a hole transporting aromatic tertiary amine moiety, X represents a divalent group, each R is a hydrogen atom or an alkyl group of, for example, from 1 to about 25 carbon atoms or an aryl group with, for example, from 6 to about 36 carbon atoms, and n represents the number of repeating segments, for example n can be a number of from about 1 to about 4.

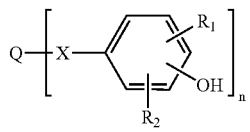

Examples of Q are arylamines selected from the group comprised of

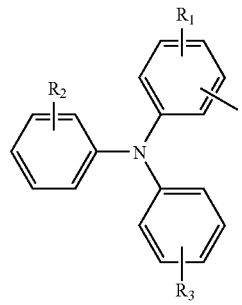
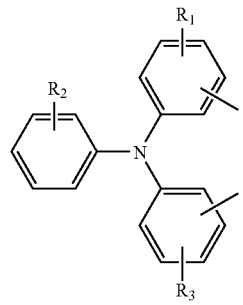
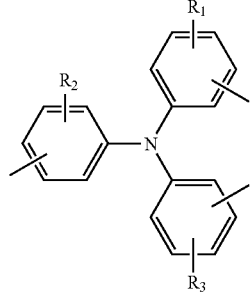
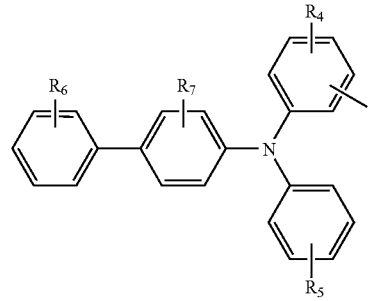
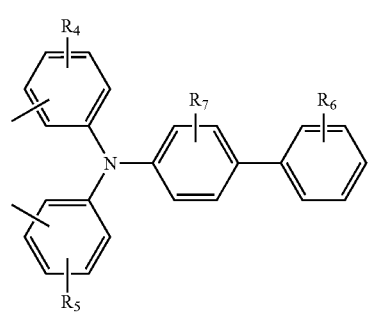

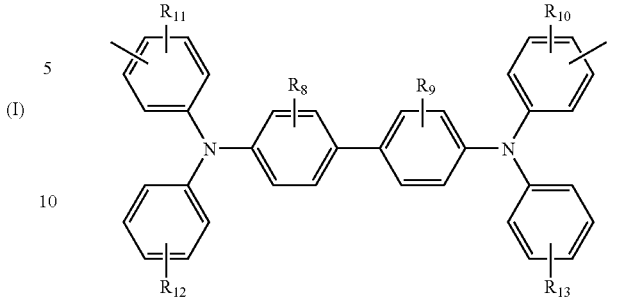
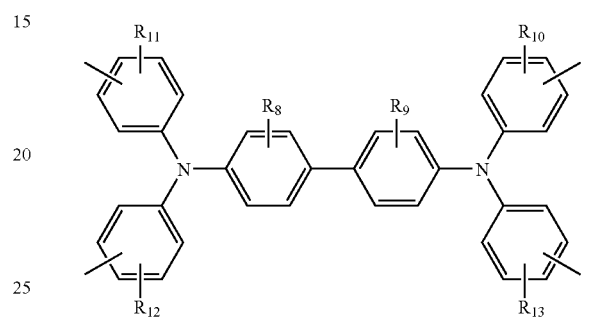
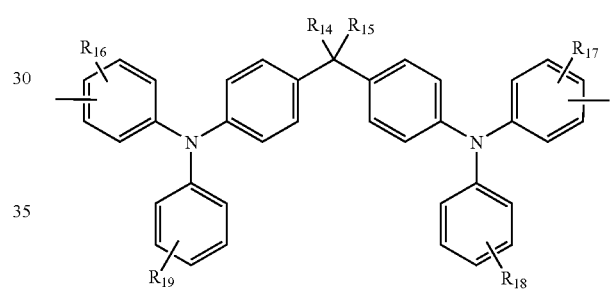
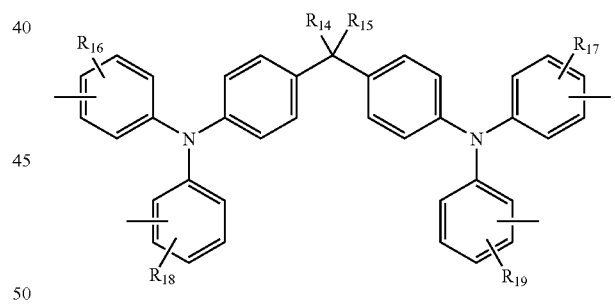

wherein $R_1$ to $R_{19}$ are independently selected from a hydrogen atom, an alkyl with from, for example, 1 to about 10 carbon atoms, a cyclic alkyl with, for example, from 1 to about 10 carbon atoms, an alkoxyl group with, for example, from 1 to about 7 carbon atoms, halogen atoms and mixtures thereof.

Examples of X are a divalent hydrocarbyl with, for example, from 1 to about 15, and more specifically, from 4 to about 12 carbon atoms, optionally further containing a heteroatom selected, for example, from the group consisting of oxygen, sulfur, silicon, and nitrogen.

Specific examples of the charge transport antioxidant components are represented by the following formulas

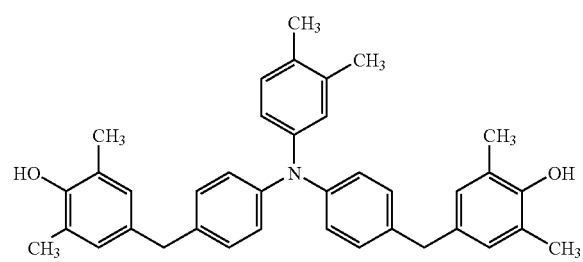
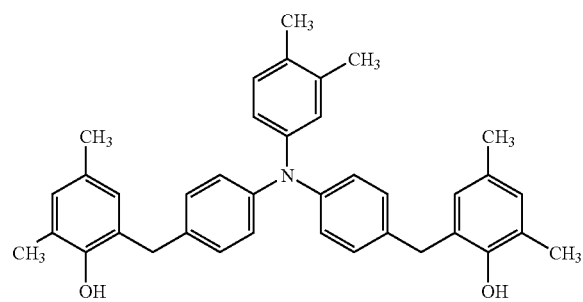
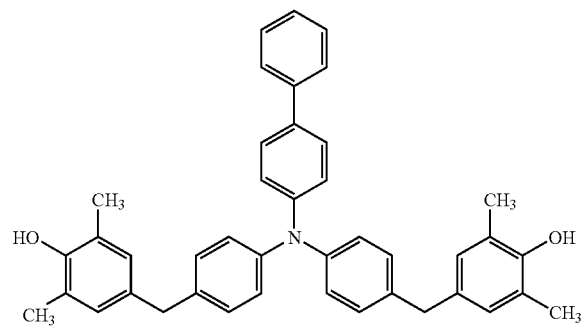
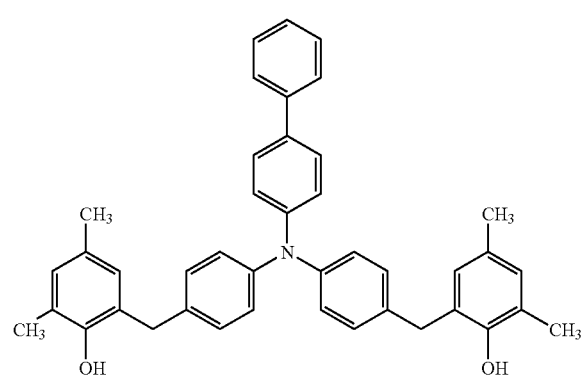
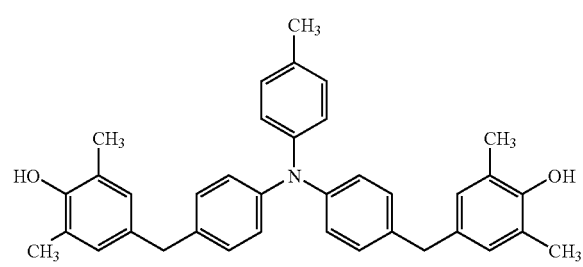
-continued
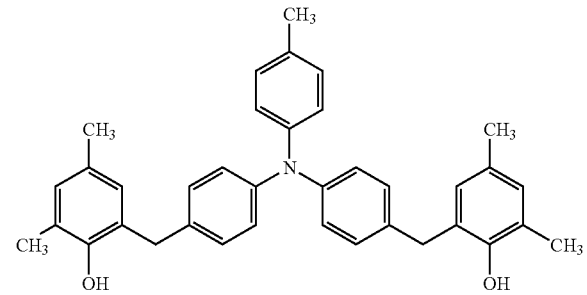
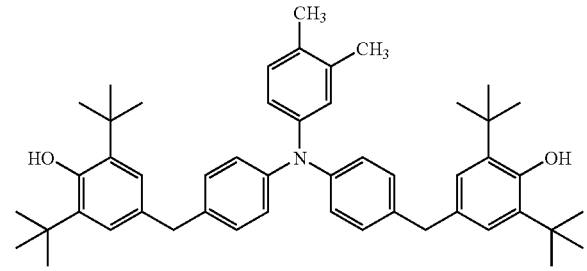
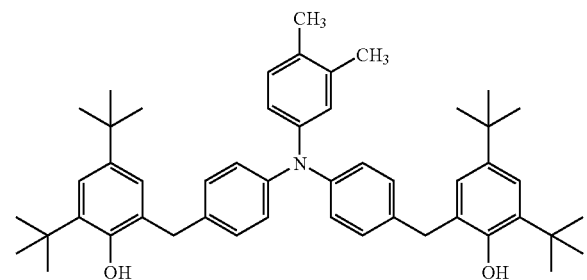
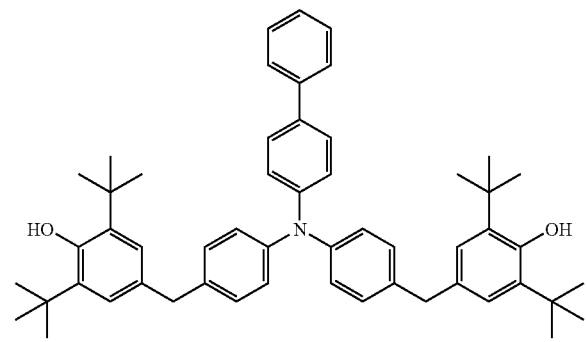
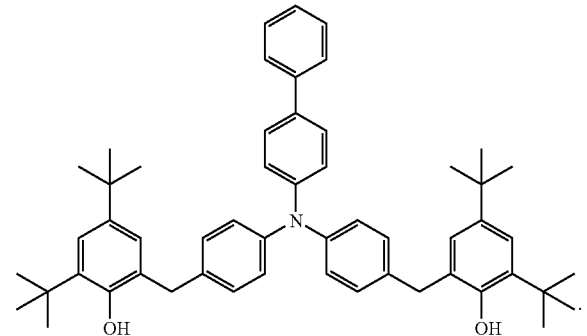

In embodiments, the photoconductive imaging member can comprise in the following sequence a supporting substrate, an adhesive layer, a photogenerating layer, and a charge transport layer, and wherein the charge transport layer is a hole transport layer. The charge, such as hole transport layer, can be generated by known methods, and more specifically, by two pass-coating processes. The hole transport molecules with a triarylamine functionality and at least one antioxidant group, such as a phenol group, are usually present in the second pass of hole transport layer with the hole transport molecules with at least one triarylamine molecule being present in the first pass. In the first pass of generating the hole transport layer, there is selected at least one of aryl amine molecules of the formula

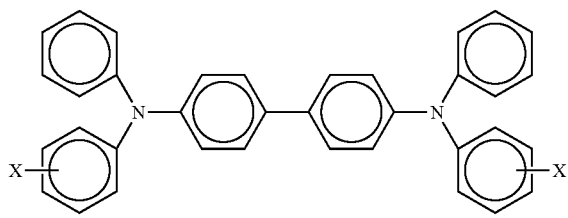

wherein X is selected from the group consisting of alkyl and halogen.

Illustrative examples of substrate layers selected for the imaging members of the present disclosure, and which substrates can be opaque or substantially transparent, comprise a layer of insulating material including inorganic or organic polymeric materials, such as MYLAR® a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass or the like. The substrate may be flexible, seamless, or rigid, and may have a number of many different configurations, such as for example, a plate, a cylindrical drum, a scroll, an endless flexible belt, and the like. In one embodiment, the substrate is in the form of a seamless flexible belt. In some situations, it may be desirable to coat on the back of the substrate, particularly when the substrate is a flexible organic polymeric material, an anticurl layer, such as for example polycarbonate materials commercially available as MAKROLON®.

The thickness of the substrate layer depends on many factors, including economical considerations, thus this layer may be of substantial thickness, for example over 3,000 microns, or of minimum thickness providing there are no significant adverse effects on the member. In embodiments, the thickness of this layer is from about 75 microns to about 300 microns.

The photogenerating layer, which can, for example, be comprised of hydroxygallium phthalocyanine Type V, is in embodiments comprised of, for example, about 60 weight percent of Type V and about 40 weight percent of a resin binder like polyvinylchloride vinylacetate copolymer such as VMCH (Dow Chemical). The photogenerating layer can contain known photogenerating pigments, such as metal phthalocyanines, metal free phthalocyanines, alkylhydroxyl gallium phthalocyanine, hydroxygallium phthalocyanines, perylenes, especially bis(benzimidazo)perylene, titanyl phthalocyanines, and the like, and more specifically, vanadyl phthalocyanines, Type V hydroxygallium phthalocyanines, and inorganic components such as selenium, selenium alloys, and trigonal selenium. The photogenerating pigment can be dispersed in a resin binder similar to the resin binders selected for the charge transport layer, or alternatively no resin binder is present. Generally, the thickness of the photogenerator layer depends on a number of factors, including the thicknesses of the other layers and the amount of photogenerator material contained in the photogenerating layers. Accordingly, this layer can be of a thickness of, for example, from about 0.05 micron to about 10 microns, and more specifically, from about 0.25 micron to about 2 microns when, for example, the photogenerator compositions are present in an amount of from about 30 to about 75 percent by volume. The maximum thickness of this layer in embodiments is dependent primarily upon factors, such as photosensitivity, electrical properties and mechanical considerations. The photogenerating layer binder resin present in various-suitable amounts, for example from about 1 to about 50, and more specifically, from about 1 to about 10 weight percent, may be selected from a number of known polymers such as poly(vinyl butyral), poly(vinyl carbazole), polyesters, polycarbonates, poly(vinyl chloride), polyacrylates and methacrylates, copolymers of vinyl chloride and vinyl acetate, phenolic resins, polyurethanes, poly(vinyl alcohol), polyacrylonitrile, polystyrene, and the like. It is desirable to select a coating solvent that does not substantially disturb or adversely affect the other previously coated layers of the device. Examples of solvents that can be selected for use as coating solvents for the photogenerator layers are ketones, alcohols, aromatic hydrocarbons, halogenated aliphatic hydrocarbons, ethers, amines, amides, esters, and the like. Specific examples are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethyl formamide, dimethyl acetamide, butyl acetate, ethyl acetate, methoxyethyl acetate, and the like.

The coating of the photogenerator layers in embodiments of the present disclosure can be accomplished with spray, dip or wire-bar methods such that the final dry thickness of the photogenerator layer is, for example, from about 0.01 to about 30 microns, and more specifically, from about 0.1 to about 15 microns after being dried at, for example, about 40° C. to about 150° C. for about 15 to about 90 minutes.

Illustrative examples of polymeric binder materials that can be selected for the photogenerator layer are as indicated herein, and include those polymers as disclosed in U.S. Pat. No. 3,121,006, the disclosure of which is totally incorporated herein by reference. In general, the effective amount of polymer binder that is utilized in the photogenerator layer ranges from about 0 to about 95 percent by weight, and preferably from about 25 to about 60 percent by weight of the photogenerator layer.

As optional adhesive layers usually in contact with the hole blocking layer, there can be selected various known substances inclusive of polyesters, polyamides, poly(vinyl butyral), poly(vinyl alcohol), polyurethane and polyacrylonitrile. This layer is, for example, of a thickness of from about 0.001 micron to about 1 micron. Optionally, this layer may contain effective suitable amounts, for example from about 1 to about 10 weight percent, of conductive and nonconductive particles, such as zinc oxide, titanium dioxide, silicon nitride, carbon black, and the like, to provide, for example, in embodiments of the present disclosure further desirable electrical and optical properties.

Examples of the binder materials for the transport layers include components, such as those described in U.S. Pat. No.

3,121,006, the disclosure of which is totally incorporated herein by reference. Specific examples of polymer binder materials include polycarbonates, acrylate polymers, vinyl polymers, cellulose polymers, polyesters, polysiloxanes, polyamides, polyurethanes, poly(cyclo olefins), and epoxies as well as block, random or alternating copolymers thereof. Preferred electrically inactive binders are comprised of polycarbonate resins with a molecular weight of from about 20,000 to about 100,000 with a molecular weight $M_w$ of from about 50,000 to about 100,000 being particularly preferred. Generally, the transport layer contains from about 10 to about 75 percent by weight of the charge transport material, and more specifically, from about 35 percent to about 50 percent of this material.

Also included within the scope of the present disclosure are methods of imaging and printing with the photoresponsive devices illustrated herein. These methods generally involve the formation of an electrostatic latent image on the imaging member, followed by developing the image with a toner composition comprised, for example, of thermoplastic resin, colorant, such as pigment, charge additive, and surface additives, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device is to be used in a printing mode, the imaging method involves the same operation with the exception that the exposure step can be accomplished with a laser device or image bar.

Moreover, in aspects thereof there is disclosed novel components and charge transport molecules of the formulas as illustrated herein, and which molecules can be prepared by the condensation of a bis(hydroxyalkylene)-triarylamine and a phenol in the presence of an acid catalyst. For example, a mixture of a di-substituted phenol such as 2,6-dimethylphenol, 2,4-dimethylphenol, 2,6-di-tert-butylphenol, 2,4-di-tert-butylphenol, and the like, a hydroxylated triarylamine such as 4,4'-dihydroxymethylene triphenylamine, 4,4'-dihydrxymethylene-4"-triphenylamine, 4,4'-dihydroxymethyl-3"4"-dimethyl-triphenylamine, and the like, and an acid catalyst such as oxalic acid, hydrochloride acid, polyphosphoric acid and the like in an amount of, for example, from about 0.5 to about 5 weight percent of the total amount of reactants, and more specifically, from about 1 to about 3 weight percent of the total amount of reactants, and optionally a small amount of solvent, such as toluene, xylene, and the like, for example from about 5 to about 20 weight percent of the total amount of reactants, more specifically from about 8 to about 15 percent of the total amount of reactants, is stirred and heated under Argon at from about 50° C. to about 120° C. The progress of this reaction is followed by thin layer chromatography (TLC); the reaction being completed in from about 1 to about 8 hours. The product can be isolated by diluting it with an organic solvent such as diethylether, toluene, methylenechloride and the like, washing the resulting solution with distilled water and then drying over sodium sulfate, followed by removing excess solvent and collecting the product with flash column chromatography. Alternatively, the resulting product can be purified by recrystallization from toluene. The yield of the reaction product is, for example, from about 33 to about 50 percent. The structure of the product resulting can be confirmed by $^1$H NMR.

A specific reaction sequence is illustrated with reference to the following

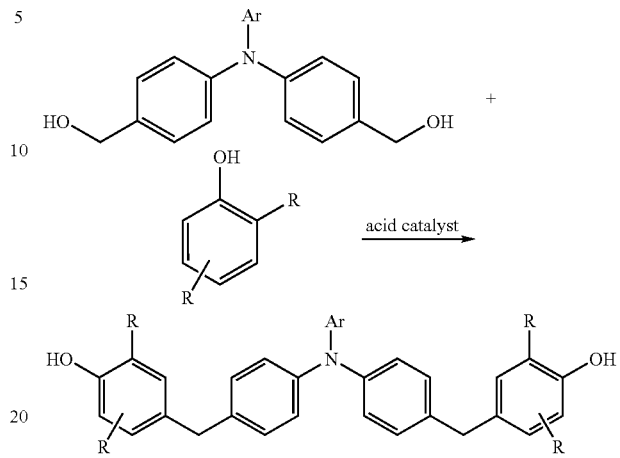

wherein the substituents are as illustrated herein.

The following Examples are being submitted to illustrate embodiments of the present disclosure. These Examples are intended to be illustrative only and are not intended to limit the scope of the present disclosure. Also, parts and percentages are by weight unless otherwise indicated. Comparative Examples and data are also provided.

EXAMPLE I

Preparation of 4,4'-bis(hydroxymethylene)-3",4"-dimethyltriphenylamine

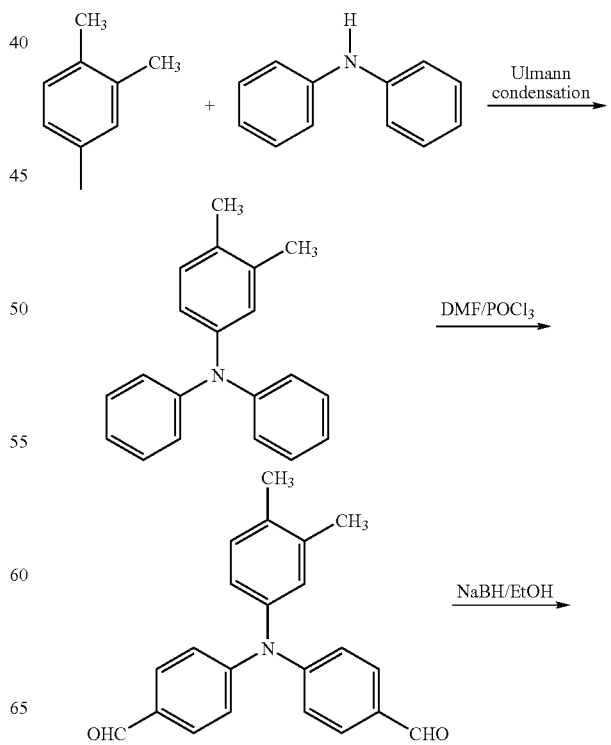

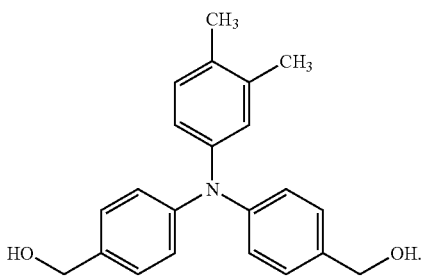

3,4-Dimethyltriphenylamine was prepared by known Ulmann condensation process.

A mixture of 3,4-dimethyl-TPA (162 grams), zinc chloride (80.76 grams), DMF (129.94 grams) and ISOPAR® L (222 grams) was charged in a 3 liter RB (round bottom) flask. Phosphorus oxychloride (272.62 grams) was added dropwise into the reaction mixture under Argon while stirring. The reaction mixture was heated to 120° C. and this temperature was maintained for 12 hours. About 500 grams of N,N'-dimethylformamide were then added to the resulting mixture. The reaction mixture was cooled to about 50° C., and poured into 2.5 liters of water with mechanical stirring. The resulting precipitates were collected by filtration and washed with water (2 liters) twice, and then refluxed in toluene with about 150 grams of an acidic clay. After the clay treatment, the toluene solution was collected and stirred with about 100 grams of silica gel at room temperature, about 23° C. to about 25° C., for 1 hour. After removal of the toluene, the product was collected and dried at 40° C. for 1 hour. The yield of the bisformal amine was 141.3 grams (71 percent).

4,4'-Bis(formal-3",4"-dimethyl-triphenylamine) obtained from the above process (139 grams) was mixed with 700 milliliters of ethanol in a 1 liter 3-neck round-bottomed flask equipped with a magnetic stirrer, and an Argon introduction tube. To the suspension resulting were added 0.1 gram of NaOH and 15.96 grams of NaBH$_4$. The reaction was conducted for 1 hour at room temperature (25° C.). The solution obtained was poured into 2.5 liters of water, and the resulting pale yellow solids were collected by filtration, and then washed with 2 liters of water. Drying at 40° C. overnight, 18 to 20 hours, generated 137 grams of crude product in 97.4 percent yield. Recrystallization in toluene (600 milliliters) and drying at room temperature under high vacuum yielded 132.8 grams of product (94.4 percent pure). The structure of the product 4,4'-bis(hydroxymethylene)-3",4"-dimethyltriphenylamine was confirmed with $^1$H NMR spectrum.

EXAMPLE II

Preparation of triarylamine-phenol Hole Transport Molecule

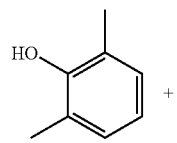

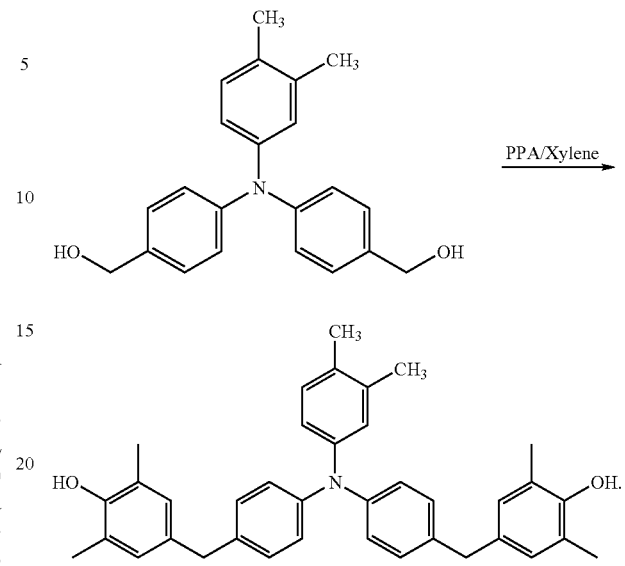

A mixture of 2,6-dimethylphenol (2.6877 grams), 4,4'-dihydroxymethylene-3",4"-dimethyl-TPA (3.3343 grams), polyphosphoric acid (20 grams) and xylene (10 milliliters) was heated in a 100 milliliter flat-bottomed flask under Argon at 120° C. The reaction was conducted for 1 hour. The resulting reaction mixture was poured into 300 milliliters of water and stirred for 12 hours. The product was collected by extraction from toluene (3×80 milliliters). The toluene layer was washed with DIW (distilled water) twice, brine once, and dried over sodium sulfate. Excess toluene was removed by roto vaporation. The product which was crystallized from the remaining liquid weighed 2.5 grams (46 percent). The structure of the above product was confirmed by $^1$H NMR spectroscopy.

EXAMPLE III

Preparation of triarylamine-phenol Hole Transport Molecule

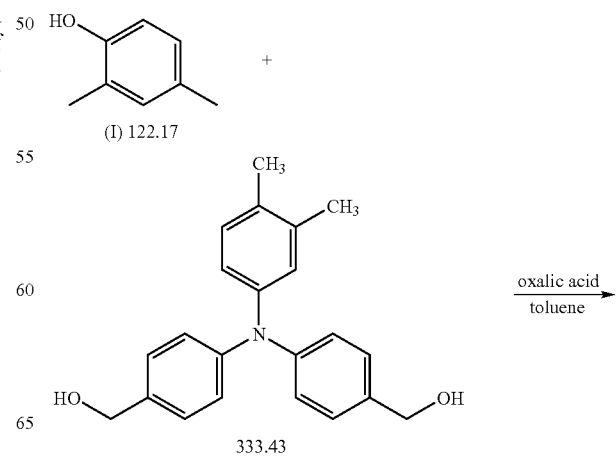

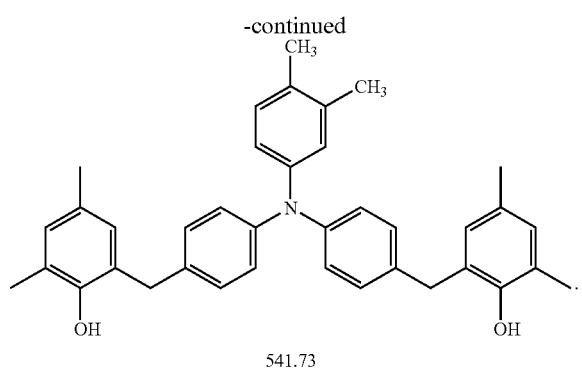

541.73

A mixture of 2,4-dimethylphenol (1.344 grams), 4,4'-dihydroxymethyl-3",4"-dimethyl-TPA (II) (1.667 grams, 5 mmole), oxalic acid (0.013 gram), and 10 milliliters of toluene was heated in a 100 milliliter flat-bottomed flask under Argon at 100° C. The reaction was conducted for 6 hours. The reaction was terminated and the mixture resulting was diluted with 20 milliliters of ether. The ether solution was washed with DIW twice until arriving at a PH of 7. After evaporation of excess solvent, the product was eluted with ¼ of acetone/hexane in a flash column. The above desired product was collected in 0.9 gram (33 percent). The structure of the product was confirmed by $^1$H NMR spectroscopy.

EXAMPLE IV

A Standard Photoreceptor Device (Control)

On a 75 micron thick titanized MYLAR® substrate was coated by draw bar technique a barrier layer formed from hydrolyzed gamma aminopropyltriethoxysilane having a thickness of 0.005 micron. The barrier layer coating composition was prepared by mixing 3-aminopropyltriethoxysilane with ethanol in a 1:50 volume ratio. The coating was allowed to dry for 5 minutes at room temperature, followed by curing for 10 minutes at 110° C. in a forced air oven. On top of the blocking layer was coated a 0.05 micron thick adhesive layer prepared from a solution of 2 weight percent of a DuPont 49K (49,000) polyester in dichloromethane. A 0.2 micron thick photogenerating layer was then coated on top of the adhesive layer with a wire wound rod from a dispersion of hydroxy gallium phthalocyanine Type V (22 parts) and a vinyl chloride/vinyl acetate copolymer, VMCH $M_n$=27,000, about 86 weight percent of vinyl chloride, about 13 weight percent of vinyl acetate and about 1 weight percent of maleic acid available from Dow Chemical (18 parts) in 960 parts of n-butylacetate, followed by drying at 100° C. for 10 minutes. Subsequently, a 24 μm thick charge transport layer (CTL) was coated on top of the above photogenerating layer by a draw bar from a solution of N,N'-diphenyl-N,N-bis(3-methylphenyl)-1,1'-biphenyl-4,4'-diamine (49.5 parts), 1 part of 2,6-di-tert-butyl-4-methylphenol (BHT) available from Aldrich Chemicals and a polycarbonate, MAKROLON® ($M_w$=52,000] available from Bayer (49.5 parts) in 667 parts of dichloromethane. The CTL was dried at 115° C. for 30 minutes.

EXAMPLE V

A Photoreceptor Device with Triarylamine-phenol Hole Transport Molecules in the Second Pass CTL was then Accomplished A photoreceptor device was prepared according to Example IV. A second CTL was coated on the top of the device from a solution of the triarylamine-phenol hole transport molecule of Example II (0.6 part) and a polycarbonate, MAKROLON® ($M_w$=52,000) available from Bayer (0.9 part), in 8.5 parts of dichloromethane. Drying the second CTL at 115° C. for 20 minutes resulted in 5 μm thick CTL. The device was subjected to evaluation of electrical and image quality.

The xerographic electrical properties of the above prepared photoconductive imaging member and other similar members can be determined by known means, including electrostatically charging the surfaces thereof with a corona discharge source until the surface potentials, as measured by a capacitively coupled probe attached to an electrometer, attained an initial value $V_o$ of about −800 volts. After resting for 0.5 second in the dark, the charged members attained a surface potential of $V_{ddp}$, dark development potential. Each member was then exposed to light from a filtered Xenon lamp thereby inducing a photodischarge which resulted in a reduction of surface potential to a $V_{bg}$ value, background potential. The percent of photodischarge was calculated as $100 \times (V_{ddp} - V_{bg})/V_{ddp}$. The desired wavelength and energy of the exposed light was determined by the type of filters placed in front of the lamp. The monochromatic light photosensitivity was determined using a narrow band-pass filter. The photosensitivity of the imaging member is usually provided in terms of the amount of exposure energy in ergs/cm$^2$, designated as $E_{1/2}$, required to achieve 50 percent photodischarge from $V_{ddp}$ to half of its initial value. The higher the photosensitivity, the smaller is the $E_{1/2}$ value. The $E_{7/8}$ value corresponds to the exposure energy required to achieve a ⅞ photodischarge from $V_{ddp}$. The device was finally exposed to an erase lamp of appropriate light intensity and any residual potential ($V_{residual}$) was measured. The imaging members were tested with a monochromatic light exposure at a wavelength of 780+/−10 nanometers, and an erase light with the wavelength of 600 to 800 nanometers and intensity of 200 ergs.cm$^2$.

Lateral image migration (LCM) was measured by the following procedure. Hand coated devices were cut into 6"×1" strips. One end of the strip was cleaned (using solvent) to expose the metallic conductive layer on the substrate. The conductivity of this layer should now have been measured to ensure that the metal had not been removed during cleaning. A multimeter was used to measure the resistance across the exposed metal layer (~1 KOhm). A fully operational 85 millimeter DC12 photoreceptor drum was prepared to expose a lengthwise strip of bare aluminum (0.5"×12"). The hand coated device was mounted onto the 8 millimeter DC12 photoreceptor drum using conductive copper tape to adhere the exposed conductive end of the device to the exposed aluminum strip on the drum thus completing a conductive path to ground. Once mounted, the device-to-drum conductivity was measured using a standard multimeter in resistance mode. The resistance between the device and the drum should be similar to the resistance of the conductive coating on the hand coated device. Once confident, the conductivity was high enough that the device ends were secured using scotch tape. All exposed conductive surfaces were covered with scotch tape. The drum was placed in the DocuColor 12 and a special template containing (1 bit, 2 bit, 3 bit, 4 bit, 5 bit) lines was printed. The machine settings (dev bias, laser power, grid bias) were adjusted to get a proper print on the hand coated devices. If the 1 bit line was barely showing, then the settings were saved and the print became the reference (pre-exposure print). The drum was removed and placed in a fume hood where specially made corotron housing was mounted onto the drum. The housing permitted a near air tight seal over the devices with the wire only a few millimeters from the devices. 500 μa (micro-amps) of current were run through the wire at 1 Hz alternating frequency for 20 minutes. The housing was then removed and the drum was placed back into the printer and another print was made which will show if any LCM has occurred. Several prints were made over lengthening time intervals to show the recovery of the exposed area on the devices.

The following table summarizes the electrical performance for these devices.

| Device | $V_{ddp}$ (−V) | $E_{1/2}$ (Ergs/cm)$^2$ | Dark Decay (V @ 500 ms) | Vr (V) | Image Quality |
|---|---|---|---|---|---|
| Control Device | 814 | 1.24 | 20 | 15 | Poor (5 minutes after exposure) |
| Device with Triarylamine-phenol in the Second Pass CTL (5 μm) | 812 | 1.32 | 17 | 29 | Good (5 minutes after exposure) |

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A photoconductive imaging member comprised of a photogenerating layer, and a charge transport layer, and wherein the charge transport layer is comprised of a resinous binder and an arylamine containing an antioxidant moiety, and wherein said arylamine containing antioxidant component is

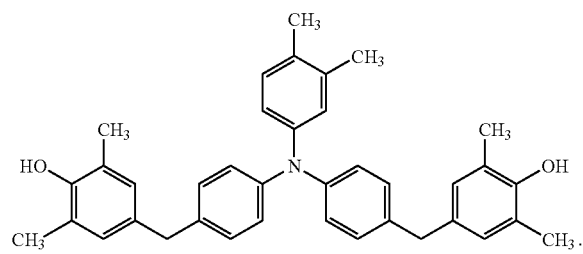

2. An imaging member in accordance with claim 1 wherein said charge transport is a hole transport that further contains a polymeric binder.

3. A photoconductive imaging member comprised of a photogenerating layer and a charge transport layer, and wherein the charge transport layer is comprised of a resinous binder and an arylamine containing an antioxidant moiety, and wherein said arylamine containing antioxidant component is of the following alternative formulas

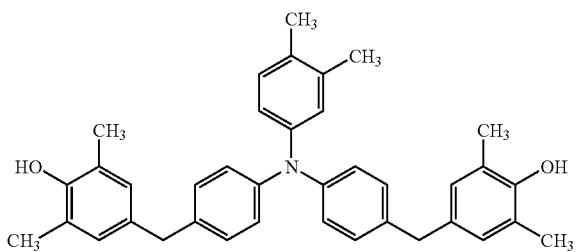

-continued

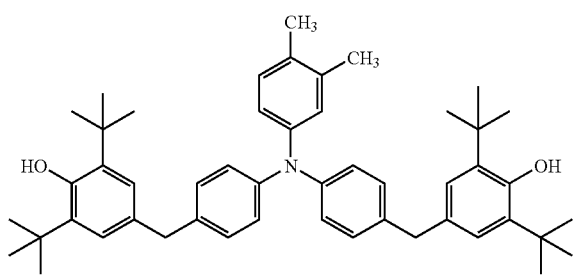

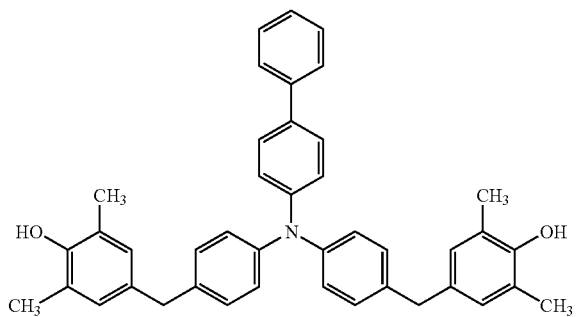

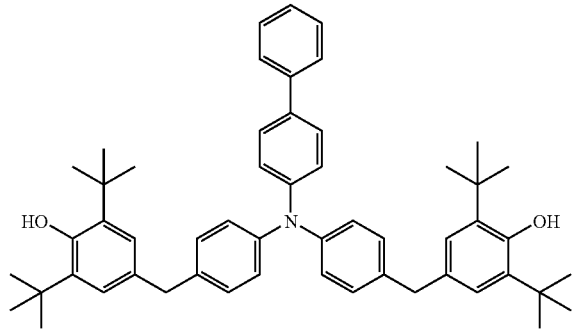

and wherein said member further contains a substrate.

4. An imaging member in accordance with claim 3 further containing a polymeric binder.

5. An imaging member in accordance with claim 3 comprised in the following sequence of a supporting substrate, said photogenerating layer, and said charge transport layer, and further containing an adhesive layer.

6. An imaging member in accordance with claim 5 wherein the adhesive layer is comprised of a polyester with an $M_w$ of about 45,000 to about 75,000, and an $M_n$ of from about 30,000 about 40,000.

7. An imaging member in accordance with claim 3 further containing a supporting substrate comprised of a conductive metal substrate of aluminum, aluminized polyethylene terephthalate or titanized polyethylene terephthalate.

8. An imaging member in accordance with claim 3 wherein said photogenerator layer is of a thickness of from about 0.05 to about 10 microns, and wherein said transport layer is of a thickness of from about 10 to about 50 microns, 9. An imaging member in accordance with claim 3 wherein the photogenerating layer is comprised of a photogenerating pigment or photogenerating pigments dispersed in a resinous binder, and wherein said pigment or pigments are present in an amount of from about 5 percent by weight to about 95 percent by weight, and wherein the resinous binder is selected from the group comprised of vinyl chloride/vinyl acetate copolymers, polyesters, polyvinyl butyrals, polycarbonates, polystyrene-b-polyvinyl pyridine, and polyvinyl formals.

10. An imaging member in accordance with claim 3 wherein the photogenerating layer is comprised of metal phthalocyanines, or metal free phthalocyanines.

11. An imaging member in accordance with claim 3 wherein the photogenerating layer is comprised of titanyl phthalocyanines, perylenes, or hydroxygallium phthalocyanines.

12. An imaging member in accordance with claim 3 wherein the photogenerating layer is comprised of Type V hydroxygallium phthalocyanine.

13. A method of imaging which comprises generating a latent image on the imaging member of claim 3, developing the image, and transferring the developed image to a suitable substrate.

14. A compound as represented by

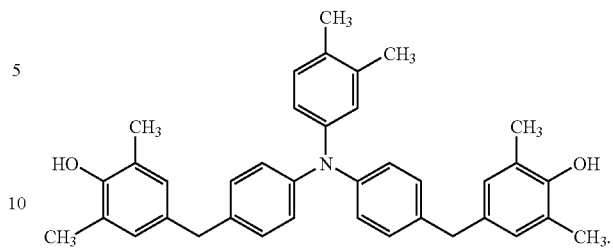

15. A photoconductive imaging member comprised of a photogenerating layer and a charge transport layer, and wherein the charge transport layer is comprised of an arylamine containing an antioxidant moiety, and wherein said arylamine contains an antioxidant of the formula

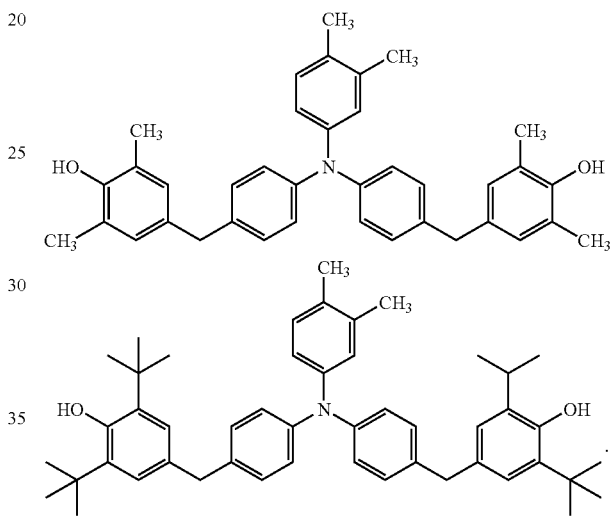

* * * * *